United States Patent
Koteles, Jr. et al.

(10) Patent No.: US 9,636,098 B2
(45) Date of Patent: May 2, 2017

(54) SURGICAL RETRACTOR WITH SPREADABLE RAKES

(71) Applicant: RULTRACT, INC., Cleveland, OH (US)

(72) Inventors: William J. Koteles, Jr., Cleveland, OH (US); Philip M. Rullo, Jr., Cleveland, OH (US)

(73) Assignee: Rultract, Inc., Cleveland, OH (US)

( * ) Notice: Subject to any disclaimer, the term of this patent is extended or adjusted under 35 U.S.C. 154(b) by 364 days.

(21) Appl. No.: 14/268,333

(22) Filed: May 2, 2014

(65) Prior Publication Data

US 2014/0330084 A1    Nov. 6, 2014

Related U.S. Application Data

(60) Provisional application No. 61/819,242, filed on May 3, 2013.

(51) Int. Cl.
   *A61B 17/02*    (2006.01)
   *A61B 17/00*    (2006.01)

(52) U.S. Cl.
   CPC ...... *A61B 17/0218* (2013.01); *A61B 17/0281* (2013.01); *A61B 17/0206* (2013.01); *A61B 2017/00367* (2013.01)

(58) Field of Classification Search
   CPC ............ A61B 17/0218; A61B 17/0281; A61B 17/0206; A61B 2017/00367
   See application file for complete search history.

(56) References Cited

U.S. PATENT DOCUMENTS

| | | | | |
|---|---|---|---|---|
| 569,839 | A | * | 10/1896 | Roeloffs ............... A61B 17/02 600/213 |
| 815,907 | A | * | 3/1906 | Davis ...................... A61B 1/32 24/514 |
| 2,002,021 | A | * | 5/1935 | Rouse ............... A61B 17/6408 606/105 |
| 2,702,540 | A | * | 2/1955 | Debeh ............... A61B 17/0231 600/218 |
| 3,750,652 | A | * | 8/1973 | Sherwin .............. A61B 17/025 600/217 |
| 4,622,955 | A |   | 11/1986 | Fakhrai |
| 4,865,019 | A | * | 9/1989 | Phillips .............. A61B 17/0206 600/232 |
| 4,881,525 | A | * | 11/1989 | Williams ............... A61B 17/02 600/217 |
| 5,176,129 | A | * | 1/1993 | Smith ................ A61B 17/0206 600/217 |

(Continued)

*Primary Examiner* — Mary Hoffman
(74) *Attorney, Agent, or Firm* — Renner, Otto, Boisselle & Sklar, LLP

(57) ABSTRACT

The present invention relates to a spreadable retractor, including a rake plate having a pair of laterally separated rake mountings; a pair of rakes, one of the rakes moveably mounted to each of the laterally separated rake mountings, wherein each of the rakes comprises a rake shaft extending away from the rake plate; and a rake spreader mounted to the rake plate at a position between the laterally separated rake mountings, the rake spreader operably linked to and configured to spread the pair of rakes apart from each other. The spreadable retractor of the present invention provides the ability for surgical personnel to use a single device to both lift and spread tissues and bones in the vicinity of a surgical incision.

15 Claims, 5 Drawing Sheets

(56) References Cited

U.S. PATENT DOCUMENTS

| | | | |
|---|---|---|---|
| 5,616,117 A * | 4/1997 | Dinkler | A61B 17/0206 600/210 |
| 5,776,054 A * | 7/1998 | Bobra | A61B 17/0206 600/210 |
| 5,899,901 A * | 5/1999 | Middleton | A61B 17/7032 606/102 |
| 5,938,592 A * | 8/1999 | Koteles | A61B 17/02 600/227 |
| 5,957,135 A | 9/1999 | Molina | |
| 5,964,699 A | 10/1999 | Rullo et al. | |
| 5,984,866 A | 11/1999 | Rullo et al. | |
| 6,083,153 A | 7/2000 | Rullo et al. | |
| 6,090,042 A | 7/2000 | Rullo et al. | |
| 6,228,026 B1 | 5/2001 | Rullo et al. | |
| 6,283,913 B1 * | 9/2001 | Seibel | A61B 1/32 600/219 |
| 6,354,994 B1 | 3/2002 | Rullo et al. | |
| 6,387,047 B1 | 5/2002 | Duhaylongsod et al. | |
| 6,488,621 B1 * | 12/2002 | Rullo | A61B 17/02 248/558 |
| 6,834,837 B2 | 12/2004 | Schilt et al. | |
| 7,097,647 B2 * | 8/2006 | Segler | A61B 17/8866 606/90 |
| 8,007,435 B2 * | 8/2011 | Hartnick | A61B 17/0206 128/200.26 |
| 2009/0259107 A1 * | 10/2009 | Crenshaw | A61B 5/0051 600/202 |

* cited by examiner

SURGICAL RETRACTOR WITH SPREADABLE RAKES

CROSS-REFERENCE TO RELATED APPLICATION

The present application is related to and claims benefit under 35 U.S.C. §119(e) to U.S. Provisional Application No. 61/819,242, filed 3 May 2013, entitled SURGICAL RETRACTOR WITH SPREADABLE RAKES, the entirety of which is hereby incorporated herein by reference.

TECHNICAL FIELD

The present invention relates to surgical retractors, more specifically to surgical retractors having spreadable rakes, and most specifically to surgical retractors having spreadable rakes adapted for use with pediatric patients, which may be referred to herein as a spreadable retractor.

BACKGROUND

Various surgical devices, including retractors, have been used for many years for lifting, holding and/or spreading body parts and surgical incisions. Known retractors, including the RULTRACT® surgical retractor described in, e.g., U.S. Pat. No. 5,964,699, are configured for lifting primarily, and if a surgical incision requires spreading as well as lifting, it has been necessary to use a separate surgical spreader device and/or one or more additional retractor. As will be readily appreciated, the more devices required to provide access to a patient's body through a surgical incision, the more complicated the procedure and the more likely problems will occur. The surgical procedure may become more complicated, for example, because the various retractor parts must by mounted in proper sequence during the course of the surgical procedure, thus extending the time required to complete the procedure. The surgical procedure may be more likely to encounter problems, e.g., in mounting the various devices, due to prolonging of the surgical procedure, making access to the incision site more difficult, and/or increasing the chances of contamination from the equipment. These potential problems are exacerbated when the patient is a pediatric patient, both due to the small size of the patient and due to the relative weakness of the patient, which may become more significant as the procedure is extended time-wise.

The incidence of re-operative median sternotomy in pediatric congenital patient population is rising. During re-sternotomy, catastrophic hemorrhage remains a dreaded complication. Anterior sternal retraction allows division of adhesions between the sternum and mediastinal structures under direct vision prior to re-sternotomy with a standard reciprocating saw. The overall mortality for redo cardiac procedures is almost 3× higher compared with first time cardiac procedures. The increased risk of redo procedure is partly related to the complications of re-sternotomy which include severe hemorrhage requiring cardiopulmonary bypass and sternal fractures. Factors associated with an increased risk of re-sternotomy include enlarged heart chamber or vessel, history of mediastinitis or sternal osteomyelitis, patent grafts and recent previous operation (<<5 years).

Thus, there has been an ongoing need for an improved surgical retractor that can combine functions, particularly for use with pediatric patients, and more specially for re-sternotomy.

SUMMARY

The present invention provides a solution to the foregoing problems by providing a surgical retractor with spreadable rakes, thus providing both lifting and spreading with the same retractor. The surgical retractor with spreadable rakes is referred to herein as a spreadable retractor.

Thus, in one embodiment, the present invention relates to a spreadable retractor, including:

a rake plate having a pair of laterally separated rake mountings;

a pair of rakes, one of the rakes moveably mounted to each of the laterally separated rake mountings, wherein each of the rakes comprises a rake shaft extending away from the rake plate; and a rake spreader mounted to the rake plate at a position between the laterally separated rake mountings, the rake spreader operably linked to and configured to spread the pair of rakes apart from each other.

In one embodiment, the rake spreader is operably linked to the pair of rakes via an elongated threaded member and a pair of spreader rings, the pair of spreader rings threadingly mounted on the elongated threaded member and operably linked to the pair of rakes.

In one embodiment, each of the spreader rings is operably linked to one of the pair of rakes by an encircling portion retaining and at least partially encircling a portion of the respective rake shaft. In one embodiment, the encircling portion is a closed ring, and in another embodiment, the encircling portion is a partially open ring.

In one embodiment, the elongated threaded member further comprises an axially enlarged centrally located wheel from which first and second portions of the elongated threaded member extend laterally outward. In one embodiment, the first and second portions are threaded in opposite directions such that when the elongated threaded member is rotated with the spreader rings attached, the spreader rings move laterally on the threaded member in opposite directions from each other. In one embodiment, the axially enlarged centrally located wheel is configured for hand rotation of the elongated threaded member.

Thus, the present invention provides an elegant solution to the problems encountered in the prior art, as will be more fully appreciated based on the following description of various embodiments of the present invention.

BRIEF DESCRIPTION OF THE DRAWINGS

The present invention may be useful with a variety of retractor apparatus. The annexed drawings are intended to provide an exemplary, non-limiting depiction of a suitable spreadable retractor apparatus and to demonstrate the disclosed invention, for the purpose of providing a better understanding of the invention, and are not intended to be limiting in any way.

Figure 1:
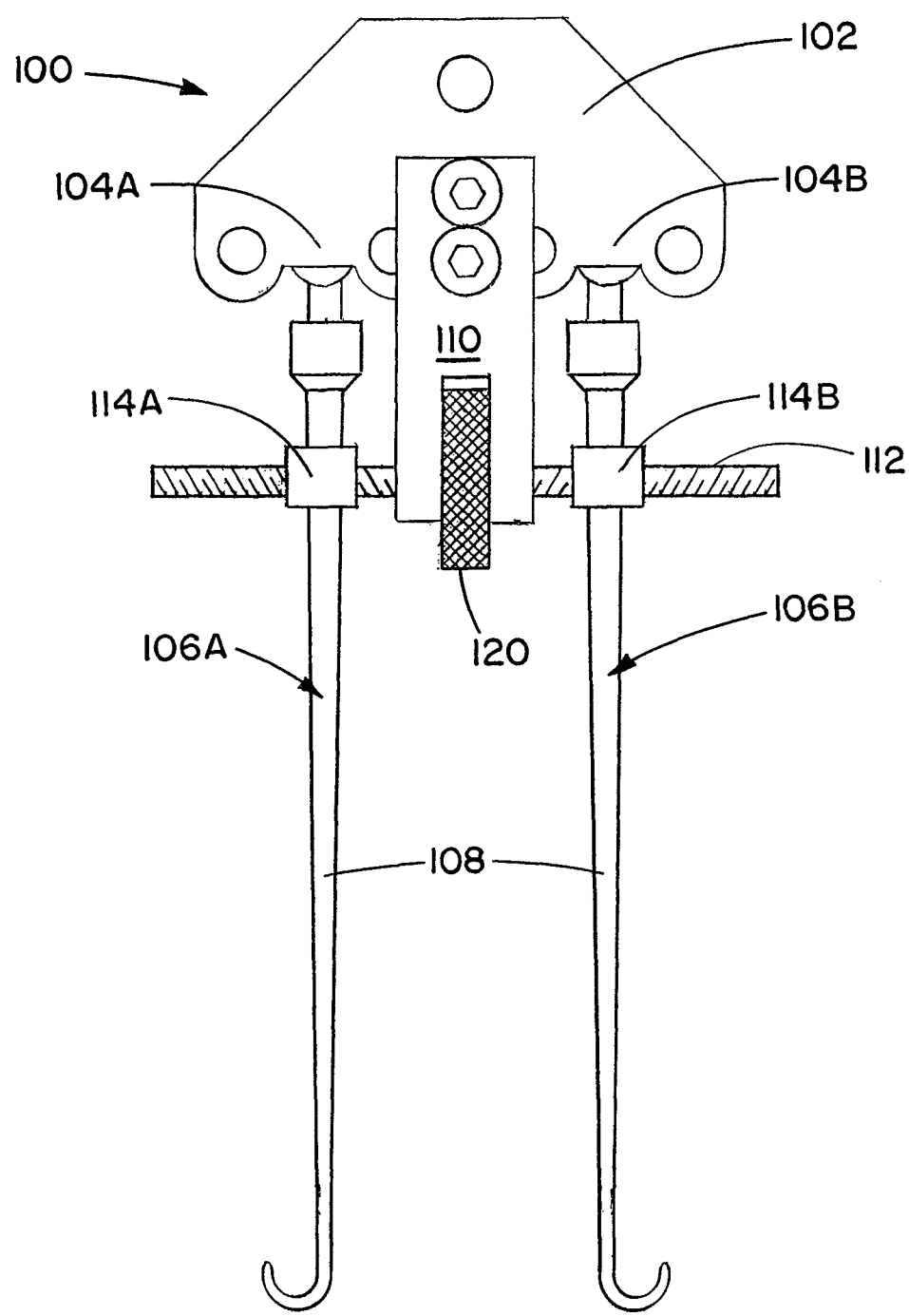
FIG. 1 is a front plan view of a spreadable retractor in accordance with an embodiment of the present invention.

It should be appreciated that for simplicity and clarity of illustration, elements shown in the Figures have not necessarily been drawn to scale. For example, the dimensions of some of the elements may be exaggerated relative to each other for clarity. Further, where considered appropriate, reference numerals have been repeated among the Figures to indicate corresponding elements.

Furthermore, it should be appreciated that the structures described herein may not provide complete specifications for producing an end-useable spreadable retractor apparatus. The present invention can be practiced in conjunction with apparatus and processing techniques currently used in the art, and only so much of the commonly practiced process steps are included as are necessary for an understanding of the present invention.

DETAILED DESCRIPTION

For redo surgery, repeat sternotomy under direct vision using the spreadable retractor in accordance with the present invention can reduce the sternotomy related morbidity (especially the need for cardiopulmonany bypass due to significant hemorrhage) and mortality.

The importance of direct visualization of the retro-sternal structures was emphasized initially by the anterior sternal retraction technique using the standard RULTRACT® retractor with a single, procedure specific rake to lift the sternum at the xiphoid, as described in U.S. Pat. No. 6,083,153, which may be consulted for additional information on this retractor, and is incorporated herein by reference for its teachings relating to the xiphoid rake and the use thereof in thoracic surgery. This retractor/rake combination creates a tunnel under the xiphoid toward the neck.

The spreadable retractor in accordance with the present invention can provide improved direct visualization and tunnel creation by lifting the sternum and spreading the sternum as the adhesions are cut away.

There are several advantages arising from the use of the spreadable retractor of the present invention. The main advantages of use this apparatus are: (1) it offers direct visualization of the anterior mediastinal vital structures; and (2) can be used as an alternative in complex cases with thick adhesions without the need to remove the posterior surface of the sternum and without any assistance other than that of the scrub nurse. This approach requires minimal previous thoracoscopic experience and, in most circumstances, after the first ten cases the operative time can be reduced significantly.

In high-risk series (patent arterial or vein grafts close to the midline), this approach may enable surgeons to undertake off-pump redo procedures in a significant proportion of surgical procedures. The combination of preservation of patent grafts and avoidance of CPB in this high-risk group has been shown to reduce morbidity and mortality.

Technical points that can facilitate dissection include the following:
1. Use of retractor/spreader device allows a progressive insertion of the blade thus keeping the same axis for insertion and vision;
2. Following the wires and dissection with diathermy away from the heart in order to avoid damage or arrhythmia is to be recommended;
3. Progressive division of the sternum can be helpful to proceed in points like the manubrium level where adhesions are usually thicker;

The application of the spreadable retractor of the present invention for ventral and cephalic traction beginning at the of the lowest part of the sternum allows for the dissection under significantly increased direct or video assisted visualization. This improved visualization continues as the dissection moves cranially until the suprasternal notch is reached. The sternal wires or other closure material are then removed and the sternum is divided using a reciprocating saw.

The lifting and coincident spreading by the spreadable retractor of the present invention both decreases the time taken to reopen the sternum and reduces the risk of factors associated with resternotomy.

It can be concluded that the spreadable retractor in accordance with the present invention will make resternotmy a safer and faster procedure.

In the following detailed description of an exemplary spreadable retractor in accordance with the present invention provides a written description of the invention sufficient to show the invention and to provide sufficient information for any person of skill in the art to make and use the invention without undue experimentation.

Figure 2:
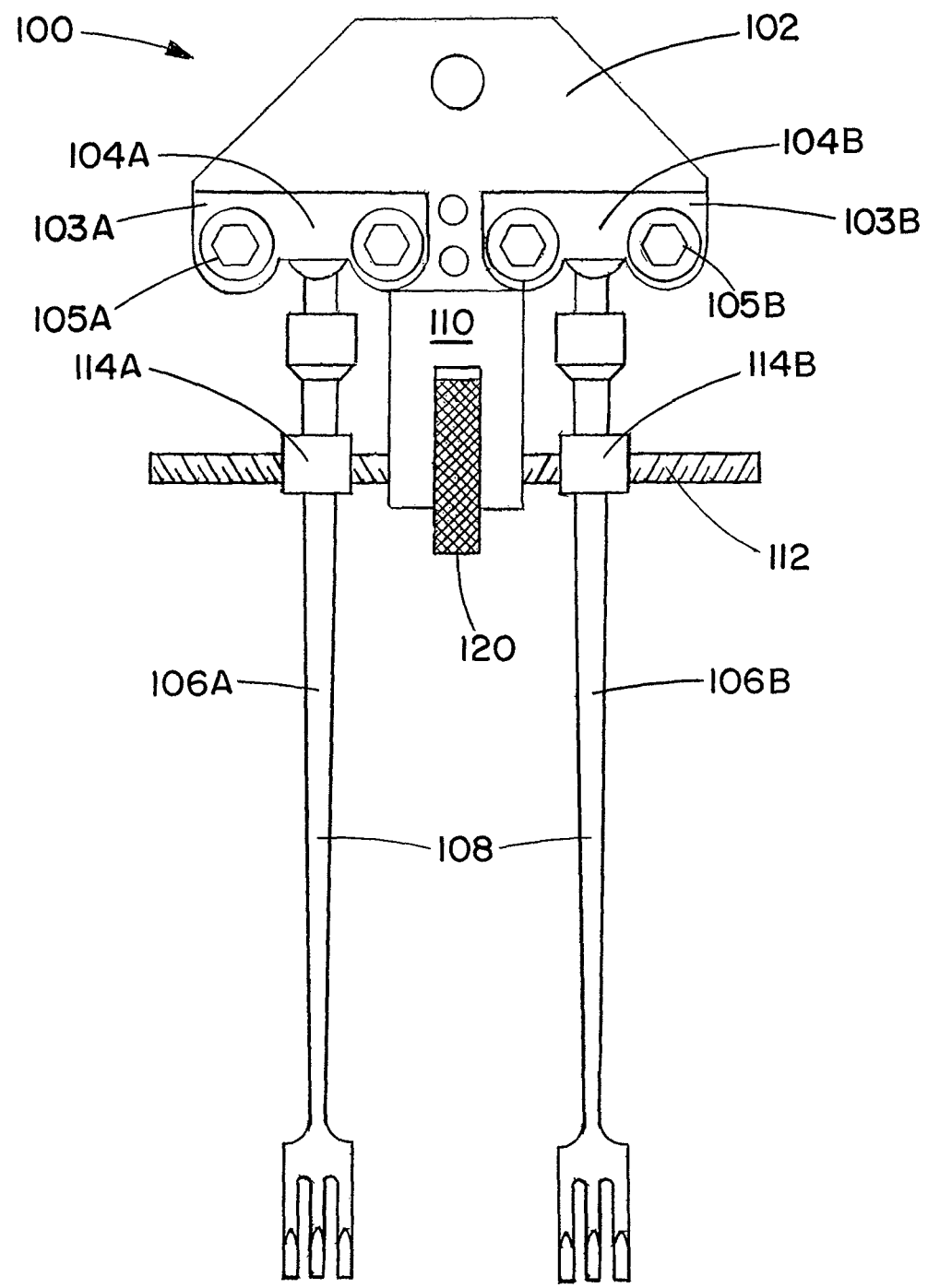
FIG. 2 is a rear plan view of a spreadable retractor in accordance with an embodiment of the present invention, such as that of FIG. 1.

In one embodiment, the present invention relates to a spreadable retractor such as that shown in FIGS. 1 and 2. As shown in FIGS. 1 and 2, there is provided a spreadable retractor 100, which includes a rake plate 102, which has a pair of laterally separated rake mountings 104A and 104B. The rake plate 102, in one embodiment, is substantially flat. The rake plate 102 may be flat, curved, Z-shape, etc., as needed and suitably selected by the skilled person. Z-shape rake plates are described in U.S. Pat. No. 5,964,699, which may be consulted for additional information on this device, and is incorporated herein by reference for its teachings relating to the Z-shape rake plate and the use thereof in thoracic surgery.

The spreadable retractor 100 in accordance with this embodiment of the present invention further includes a pair of rakes 106A and 106B. As shown in FIGS. 1 and 2, in accordance with this embodiment, one of the rakes 106A, 106B, is moveably mounted to each of the laterally separated rake mountings 104A, 104B. The mounting will be described in more detail below. As shown in FIGS. 1 and 2, each of the rakes 106A, 106B, includes a rake shaft 108 extending away from the rake plate 102.

The retractor in accordance with the present invention further includes a rake spreader assembly 110 mounted to the rake plate 102. As shown in FIGS. 1 and 2, the rake spreader assembly 110 may be mounted at a position between the laterally separated rake mountings 104A, 104B. In accordance with the invention, the rake spreader 110 is operably linked to and is configured to spread the pair of rakes 106A, 106B, apart from each other, as well as to bring the pair of rakes 106A, 106B, towards each other, as needed.

As shown in FIGS. 1 and 2, in this embodiment, in the spreadable retractor 100, the rake spreader assembly 110 includes, and is operably linked to the pair of rakes 106A, 106B via, an elongated threaded member 112 and a pair of spreader rings 114A, 114B. The pair of spreader rings 114A, 114B are threadingly mounted on the elongated threaded member 112 and thereby are operably linked to the pair of rakes 106A, 106B, respectively.

Figure 3A:
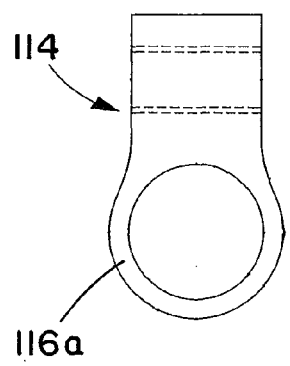
FIGS. 3A and 3B are top plan views and 3C is a side elevation view of embodiments of spreader rings in accordance with embodiments of the present invention.
Figure 3B:
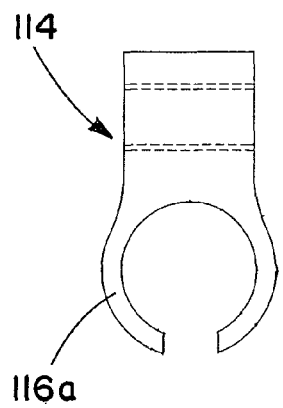

As shown in FIGS. 1 and 2, the spreadable retractor 100 includes the spreader rings 114A, 114B, and, as shown in FIGS. 3A and 3B, each of the spreader rings is operably linked to one of the pair of rakes 106A, 106B by an encircling portion 116. The encircling portion 116 retains and at least partially encircles a portion of the respective rake shaft 108.

As best shown in FIG. 2, the laterally separated rake mountings 104A, 104B are formed by the rake plate 102 and a suitably mounted rake mounting plate 103A and rake mounting plate 103B, on each side of the rake plate 102. The rake plate 102 and the rake mounting plates 103A, 103B may include suitably-shaped indentations into which an upper portion of the rakes 106A, 106B may be retained. This retention may be accomplished by, e.g., a ball-and-socket fitting, which would have the advantage of allowing the rakes 106A, 106B to undergo some degree of independent rotation, or by a pin-receptacle fitting, with which the rakes 106A, 106B would be allowed to undergo only back-and-forth movement in a single plane, rather than more freely swiveling in more than one plane as with the ball-and-socket fitting. Other suitable fittings by which the rakes 106A, 106B are securely retained in the rake mountings 104A, 104B may be suitably selected or devised by the skilled person.

As best shown in FIG. 2, the rake mounting plates 103A, 103B are securely attached to the rake plate 102 via a suitable attachment means, such as a bolt/nut arrangement 105A, 105B shown in FIG. 2, a bolt/threaded rake plate arrangement (not shown), a rivet (not shown), or other suitable attachments known in the art.

As shown in FIG. 3A, in one embodiment of the spreader rings 114, the encircling portion 116 is a closed ring. In this embodiment, the closed ring completely surrounds the rake shaft 108.

As shown in FIG. 3B, in another embodiment of the spreader rings 114, the encircling portion 116a is a partially open ring. The partially open ring 116a is sufficiently closed to retain the rake shaft 108, even though it does not completely surround the rake shaft 108. The partially open ring 116a may be manufactured by simply bending metal parts, instead of machining or casting, which might be required to form the closed ring of the encircling portion 116.

Figure 3C:
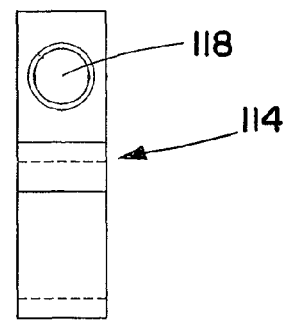

FIG. 3C is a side elevation view of the spreader ring 114. As shown in FIG. 3C, in one embodiment, the spreader ring 114 includes a hollow, threaded female opening through which the threaded portion 112 passes and operably functions to move the spreader ring 114 laterally along the longitudinal axis of the threaded portion 112 as the threaded portion 112 is rotated. This lateral movement of the spreader rings 114 along the longitudinal axis of the threaded portion 112 functions to move the rakes 106A, 106B outward, and thus to spread the rakes, in accordance with the present invention. As will be understood, rotating the threaded portion 112 in the opposite direction causes the rakes 106A, 106B to move toward each other and thus reverses the spreading action described above.

Figure 4:
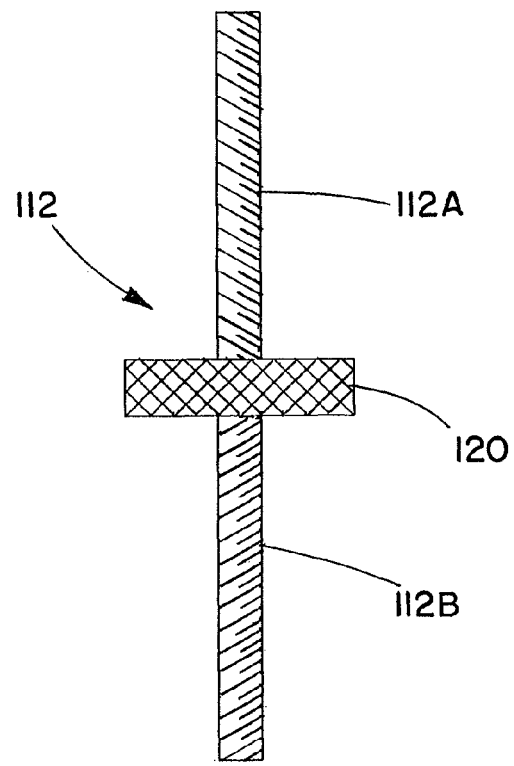
FIG. 4 is a side elevation view of an elongated threaded member in accordance with an embodiment of the present invention.
Figure 5:
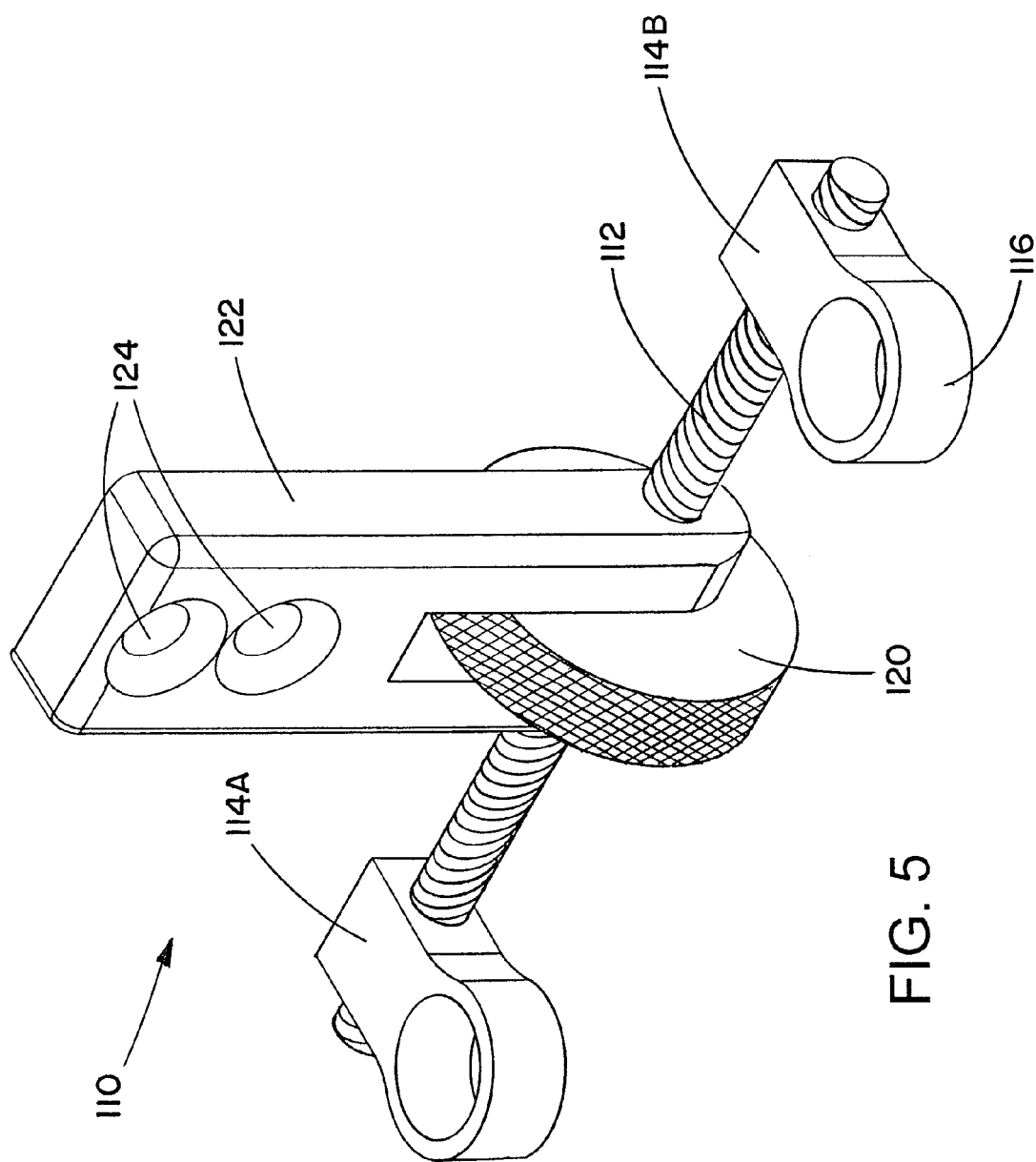
FIG. 5 is a front side perspective view of a spreader assembly in accordance with an embodiment of the present invention.

As shown in FIGS. 1, 2 and 4, in one embodiment, the elongated threaded member 112 further comprises an axially enlarged centrally located wheel 120 from which first portion 112A and second portion 112B of the elongated threaded member 112 extend laterally outward. The wheel 120, as shown in FIGS. 4 and 5, is round. However, the wheel 120 need not be round, but may be configured in any suitable shape, as determined by the skilled person. The wheel 120 should have a shape and diameter suitable and adapted to provide easy rotation of the elongated threaded member 112 by surgical personnel during a surgical procedure. Thus, the outer periphery of the wheel 112 may be, for example, round, square, hexagonal, octagonal or other suitable multi-sided shape, etc. As noted, the surface of the wheel 120 may be knurled, roughened, or otherwise suitably textured to enable the easy rotation of the elongated threaded member 112.

As best shown in FIG. 4, the first and second portions 112A, 112B, are threaded in opposite directions such that when the wheel 120 is rotated causing the elongated threaded member 112 to rotate with the spreader rings 114 attached, the spreader rings 114 move laterally on the threaded member 112 in opposite directions from each other. In one embodiment, as shown in the figures, the wheel 120 is configured for hand rotation of the elongated threaded member, by having a knurled, roughened or otherwise textured surface that enables surgical personnel to easily rotate the elongated threaded member 112 thereby to spread the rakes 106A, 106B apart from each other, and to draw the rakes 106A, 106B, back towards each other as needed during a surgical procedure.

FIG. 5 is a front side perspective view of the spreader assembly 110 in accordance with an embodiment of the present invention. The spreader assembly 110 includes a base plate 122, which is provided with one or more, preferably, two, openings 124, adapted to receive a bolt, rivet or other attachment means, by which the base plate 122 is attached to the rake plate 102. Suitable exemplary attachment means are illustrated in FIGS. 1 and 2. The spreader assembly 110, as described with respect to FIGS. 1 and 2, includes, and is operably linked to the pair of rakes 104A, 104B via, an elongated threaded member 112 and a pair of spreader rings 114A, 114B. The pair of spreader rings 114A, 114B are threadingly mounted on the elongated threaded member 112 and thereby are operably linked to the pair of rakes 106A, 106B, respectively. In the embodiment illustrated in FIG. 5, the spreader rings 114A, 114B include the closed rings 116, as described with respect to FIG. 3A.

It is noted that the elongated threaded member is fixedly attached to the wheel 120, so that when the wheel 120 is rotated, the elongated threaded members are rotated, thus causing the both of the spreader rings 114A, 114B to move outwardly or inwardly at the same time. Thus, in the embodiment shown in FIGS. 1 and 2, when the spreader rings 114A, 114B move outwardly, the rakes 106A, 106B are forced to move outwardly, and when the spreader rings 114A, 114B move inwardly, the rakes 106A, 106B are forced to move inwardly, as a result of the rotation of the wheel 120.

Figure 6:
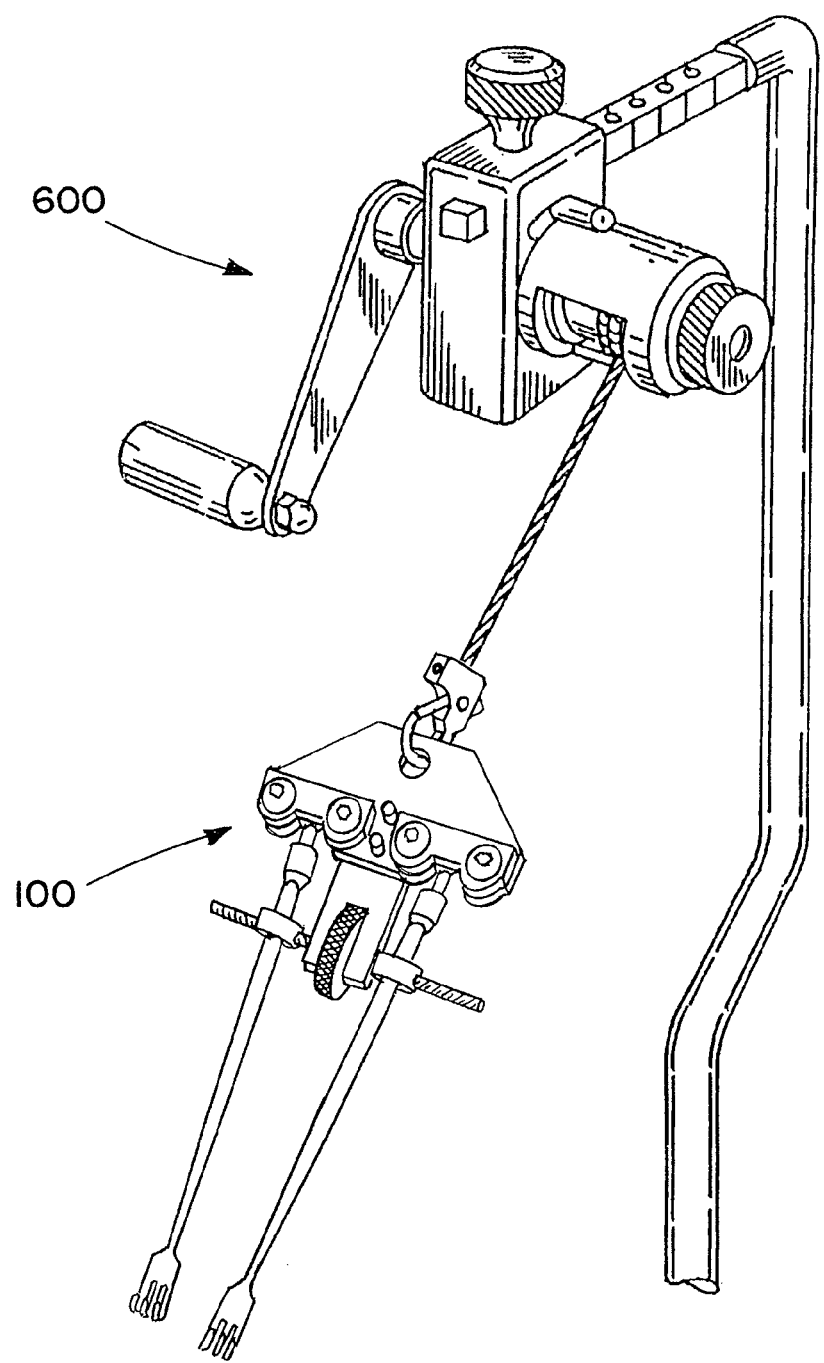
FIG. 6 is a perspective view of an exemplary conventional retractor apparatus operably attached to a spreadable retractor in accordance with an embodiment of the present invention.

FIG. 6 is a perspective view of an exemplary retractor apparatus 600, such as the RULTRACT® retractor apparatus, with a spreadable retractor 100 in accordance with an embodiment of the present invention, attached in position for operation. The retractor apparatus 600 may be any suitable retractor apparatus known in the art, and is not limited to the RULTRACT® retractor apparatus.

While the principles of the invention have been explained in relation to certain particular embodiments, these embodiments are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A spreadable retractor, comprising:
   a rake plate having a pair of laterally separated rake mountings;
   a pair of rakes, one of the rakes moveably mounted to a respective one of the laterally separated rake mountings, wherein each of the rakes comprises a rake shaft extending away from the rake plate; and
   a rake spreader mounted to the rake plate at a position between the laterally separated rake mountings, the rake spreader operably linked to and configured to spread the pair of rakes apart from each other, the rake spreader comprising a single centrally located wheel attached to the rake spreader,
   wherein the rake spreader is operably linked to the pair of rakes via an elongated threaded member and a pair of spreader rings, the pair of spreader rings threadingly mounted on the elongated threaded member and operably linked to the pair of rakes, and
   wherein each of the spreader rings is operably linked to one of the pair of rakes by an encircling portion retaining and at least partially encircling a portion of the respective rake shaft.

2. The spreadable retractor of claim 1 wherein the encircling portion is a closed ring.

3. The spreadable retractor of claim 1 wherein the encircling portion is a partially open ring.

4. The spreadable retractor of claim 1 wherein the single, centrally located wheel is axially enlarged and from which first and second portions of the elongated threaded member extend laterally outward.

5. A spreadable retractor, comprising:
   a rake plate having a pair of laterally separated rake mountings;
   a pair of rakes, one of the rakes moveably mounted to each of the laterally separated rake mountings, wherein each of the rakes comprises a rake shaft extending away from the rake plate; and
   a rake spreader mounted to the rake plate at a position between the laterally separated rake mountings, the rake spreader operably linked to and configured to spread the pair of rakes apart from each other,
   wherein the rake spreader is operably linked to the pair of rakes via an elongated threaded member and a pair of spreader rings, the pair of spreader rings threadingly mounted on the elongated threaded member and operably linked to the pair of rakes,
   wherein the elongated threaded member further comprises an axially enlarged centrally located wheel from which first and second portions of the elongated threaded member extend laterally outward, and
   wherein the first and second portions are threaded in opposite directions such that when the elongated threaded member is rotated with the spreader rings attached, the spreader rings move laterally on the threaded member in opposite directions from each other.

6. A spreadable retractor, comprising:
   a rake plate having a pair of laterally separated rake mountings;
   a pair of rakes, one of the rakes moveably mounted to a respective one of the laterally separated rake mountings, wherein each of the rakes comprises a rake shaft extending away from the rake plate; and
   a rake spreader mounted to the rake plate at a position between the laterally separated rake mountings, the rake spreader operably linked to and configured to spread the pair of rakes apart from each other, the rake spreader comprising a single centrally located wheel attached to the rake spreader,
   wherein the rake spreader is operably linked to the pair of rakes via an elongated threaded member and a pair of spreader rings, the pair of spreader rings threadingly mounted on the elongated threaded member and operably linked to the pair of rakes
   wherein the single, centrally located wheel is axially enlarged and from which first and second portions of the elongated threaded member extend laterally outward
   wherein the axially enlarged centrally located wheel is configured for hand rotation of the elongated threaded member.

7. The spreadable retractor of claim 1 wherein the single, centrally located wheel is attached to the elongated threaded member from which first and second portions of the elongated threaded member extend laterally outward.

8. The spreadable retractor of claim 7 wherein the first and second portions are threaded in opposite directions such that when the elongated threaded member is rotated with the spreader rings attached, the spreader rings move laterally on the threaded member in opposite directions from each other.

9. The spreadable retractor of claim 7 wherein the axially enlarged centrally located wheel is configured for hand rotation of the elongated threaded member.

10. The spreadable retractor of claim 2 wherein the single, centrally located wheel is attached to the elongated threaded member from which first and second portions of the elongated threaded member extend laterally outward.

11. The spreadable retractor of claim 10 wherein the first and second portions are threaded in opposite directions such that when the elongated threaded member is rotated with the spreader rings attached, the spreader rings move laterally on the threaded member in opposite directions from each other.

12. The spreadable retractor of claim 10 wherein the axially enlarged centrally located wheel is configured for hand rotation of the elongated threaded member.

13. The spreadable retractor of claim 3 wherein the single, centrally located wheel is attached to the elongated threaded member from which first and second portions of the elongated threaded member extend laterally outward.

14. The spreadable retractor of claim 13 wherein the first and second portions are threaded in opposite directions such that when the elongated threaded member is rotated with the spreader rings attached, the spreader rings move laterally on the threaded member in opposite directions from each other.

15. The spreadable retractor of claim 13 wherein the axially enlarged centrally located wheel is configured for hand rotation of the elongated threaded member.

* * * * *